United States Patent [19]

Pickering et al.

[11] 4,240,410
[45] Dec. 23, 1980

[54] OPHTHALMIC ELECTROMAGNET

[75] Inventors: Norman C. Pickering, Sag Harbor; Yale Fisher, New York, both of N.Y.

[73] Assignee: Storz Instrument Company, St. Louis, Mo.

[21] Appl. No.: 6,080

[22] Filed: Jan. 23, 1979

[51] Int. Cl.³ ............................................... A61B 17/52
[52] U.S. Cl. .................................................... 128/1.5
[58] Field of Search ................................... 128/1.4, 1.5

[56] References Cited

U.S. PATENT DOCUMENTS

| 591,160 | 10/1897 | Dow | 128/1.4 |
| 1,831,280 | 11/1931 | Wright | 128/1.4 |
| 2,321,356 | 6/1943 | Berman | 128/1.4 |
| 2,436,538 | 2/1948 | Wing, Sr. | 128/1.4 |

*Primary Examiner*—William E. Kamm
*Attorney, Agent, or Firm*—Robert A. Kelly

[57] ABSTRACT

A miniature surgical instrument that is particularly useful for removing ferrous foreign particles from an eye, includes a housing and a wire wound coil positioned within the housing. A magnetizable, axially elongated probe includes a first tip portion that is positioned externally of the housing and a second, body portion that is within the housing and which is surrounded by the coil. A switch is coupled to the coil and is adapted to interconnect the coil to a source of electrical energy so that when the switch means is operated the coil is energized and the probe is magnetized.

9 Claims, 2 Drawing Figures

OPHTHALMIC ELECTROMAGNET

BACKGROUND OF THE INVENTION

1. Field of the Invention

This invention relates generally to surgical instruments and more particularly to a miniature surgical instrument that is adapted to remove ferrous foreign particles from an eye.

2. Description of the Prior Art

Generally speaking, intraocular foreign bodies may classified as either magnetic or non-magnetic. The present invention is directed only to the former type and only that form of prior art will be discussed.

Magnets have been used for some time in the removal of ferrous foreign objects in the eye. However, prior art structures have not been entirely satisfactory. One technique which has been used for many years is to locate the foreign body and to manipulate it by means of a relatively large magnet or electromagnet that is applied outside the eye. When the ferrous particle is brought near the surface an incision is made in the sclera and the particle is removed either by forceps or by the magnet. Several problems are related to this technique. For example, it may be necessary to remove one or more extra-ocular muscles in order to reach the operating site. Furthermore, damage may be done to the retina by removing the body through the wall of the eye, or damage may be done to the vitreous in moving the foreign body within the eye by the external magnet. In addition, it is frequently difficult to determine exactly where to cut the sclera in order to position the extracting tool directly over the foreign body and in such instances it is not uncommon that a larger incision than is absolutely necessary must be made.

The earliest magnets that were used for the purpose of removing a ferrous foreign object from the eye were permanent magnets. However, with such type instruments, it was necessary for the ferrous foreign body to be virtually in contact with the pole tip of the magnet in order to remove the object. In order to determine the efficiency of an electromagnet that is used for the purpose of removing ferrous foreign bodies, the field strength and the gradient of the field strength must be determined. It is well known that the magnetic field of an electromagnet can magnetize a foreign body that is made of ferrous material and which is located in the eye. The gradient of the field strength of the magnet serves to pull the ferrous object towards the pole tip during that portion of time when the ferrous particle approaches the magnet.

Another form of eye repair damage by foreign objects requires the surgeon to work within the eye through a pair of needle insertions that are less than 1 mm. in diameter. In one of the insertions, a bundle of glass fibers conducts light into the eye. Through the other insertion a series of surgical instruments can be inserted to work within the eye. In many cases a jell-like vitreous humor is removed and is replaced with a saline solution. After such a procedure the interior of the eye is optically cleared and the surgeon is able to see inside. When the foreign body is visable, for example it may be resting against the retina, the surgeon can then insert the tip of the probe comprising the present invention through one of the needle holes in the eye and bring it close to the ferrous particle. By pressing the button on the present invention a switch is closed and a coil is electrically energized so as to magnetize the tip of the probe to thereby cause the ferrous foreign body to adhere to the probe. Subsequently the foreign particle can be removed. If further manipulation is required releasing of the button demagnetizes the tip of the probe and the foreign body can easily be transferred to forceps or another instrument.

SUMMARY OF THE INVENTION

Briefly, the present invention provides an elongated housing of miniature size. A magnetizable, axially elongated probe is partially positioned within the housing. The tip portion of the probe extends outwardly while the body portion of the probe is contained within the housing and is surrounded by an electrical coil that is coupled to a switch that is interconnected to a source of electrical energy such as a battery that may also be contained within the surgical instrument. Thus, when the push button of the switch is depressed, the coil is energized and the tip of the probe is magnetized so that it may be used in the manner described hereinabove.

Accordingly, it is an object of the present invention to provide an improved miniature surgical instrument that is adapted for removing ferrous foreign particles from an eye.

Another object of the present invention is to provide a miniature surgical instrument, as described above, having an axially elongated probe that may be magnetized and demagnetized by the depression of a push button which actuates a switch.

Still another object of the present invention is to provide a miniature surgical instrument, as described above, wherein the tip portion of the probe is hemispherical.

A further object of the present invention is to provide a miniature surgical instrument, as described above, werein the tip portion of the probe is approximately 1.0 mm in diameter.

Yet another object of the present invention is to provide a miniature surgical instrument, as described above, having a self contained-source of electrical energy.

These and other objects, features and advantages of the invention will, in part, be pointed out with particularity, and will, in part become obvious from the following more detailed description of the invention, taken in conjunction with the accompanying drawing which forms an integral part thereof.

BRIEF DESCRIPTION OF THE DRAWING

In the various figures of the drawing, like reference characters designate like parts.

In the drawing.

DESCRIPTION OF THE PREFERRED EMBODIMENT

Figure 1:
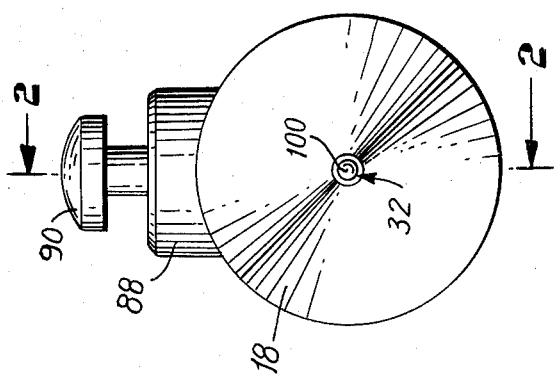
FIG. 1 is a front view of the miniature surgical instrument comprising the present invention.
Figure 2:
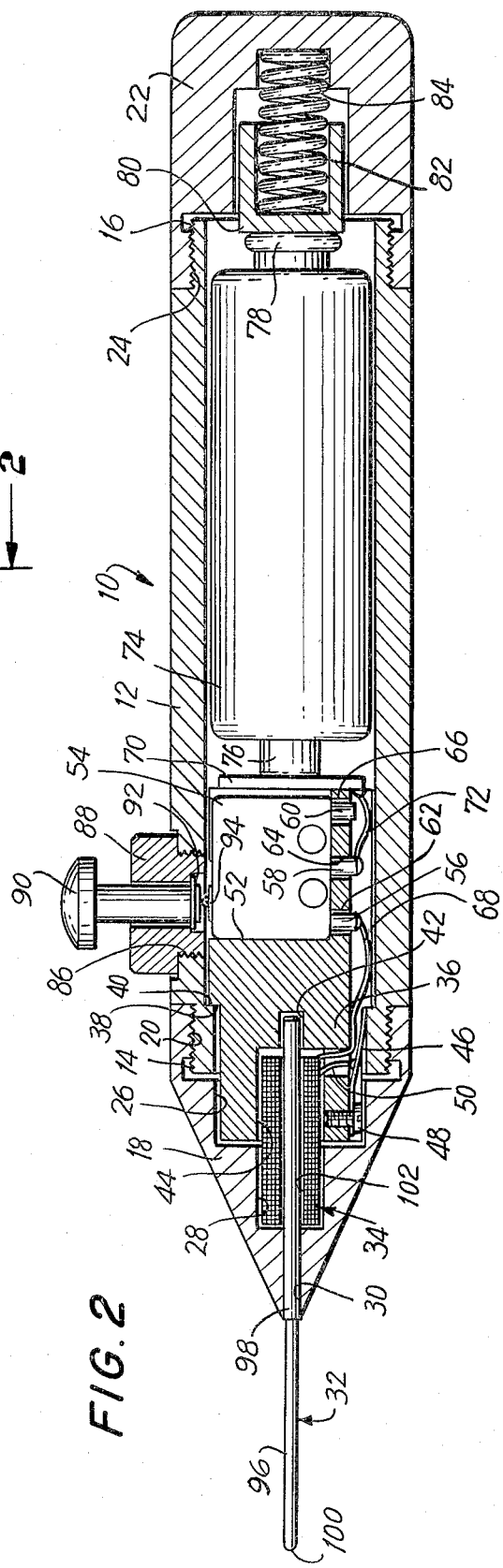
FIG. 2 is a longitudinal, sectional, elevational view taken along line 2—2 of FIG. 1.

Referring now to the drawing, there is shown a miniature surgical instrument 10 comprising the present invention. The instrument 10 includes a hollow housing 12 having external threads 14 and 16 at the forward and rearward ends thereof, respectively. A conical sleeve 18 having internal threads 20 is removably secured to the threaded end 14 of the housing 10. Similarly, an end cap 22 having internal threads 24 is removably secured to the external threads 16 at the rearward end of the housing 12.

The conical sleeve 18 is provided with three coaxial and concentric bores 26, 28 and 30. In a manner to be described more fully hereinafter, a probe generally designated by the reference character 32 is contained within the bore 30. An electrical coil, generally designated by the reference character 34, is contained within the bore 28 and a plug, generally designated by the reference character 36, is contained within the bore 26.

The plug 36 is provided with a transverse shoulder 38 which abuts an internal, transverse wall 40 formed within the housing 12 proximate the forward end thereof. The coaction of the shoulder 38 and the wall 40 limit forward movement of the plug 36. First and second bores 42 and 44, respectively, serve to receive the rearward end of the probe and a portion of the coil 34. A metallic strap 46 that is used for grounding purposes is secured to the plug 36 by means of a set screw 48. The coil 34 is electrically connected to the strap 46 by means of a conductive lead 50. The end of the strap 46 that is remote from the set screw 48 bears against an internal portion of the housing 12 which is made of a metallic material. The plug 36 is provided with a seat 52 at its rearward end for the purpose of receiving a switch member 54. In the embodiment illustrated, the switch member 54 includes three terminals 56, 58 and 60 which extend through openings 62, 64 and 66, respectively, that are formed in the rearward end of the plug 36. The coil 34 is also electrically coupled to the terminal 56 of the battery 54 by means of a conductive lead 68. Terminal 58 of the switch 54 is electrically coupled to a metallic plate 70 by means of a conductive lead 72.

A battery 74 is contained within the housing 12 and is provided with terminals 76 and 78 at the forward and rearward ends thereof, respectively. The terminal 76 bears against the metallic plate 70. At its opposite end, the terminal 78 of the battery 74 bears against a cup-shaped retainer 80 which contains a compression spring 82. A recess 84 formed in the end cap 22 receives the opposite end of the compression spring 82. Thus, the battery 74 is continuously urged in a forward direction so that the terminal 76 always bears against the plate 70 and so that the terminal 78 is always in intimate electrical contact with a portion of the housing 12.

The housing 12 further includes a tapped hole 86 that is arranged to receive a collar 88 through which a push button 90 is inserted. A retaining ring 92 limits the push button 90 to inward movement only so that the contact button 94 of the switch 54 may be depressed manually.

Turning now to the probe 32, it will be seen that there is provided a tip portion 96 and a body portion 98 that is somewhat larger in diameter than the tip portion 96. Furthermore, the tip portion 96 terminates in a hemispherical end 100. One section of the body portion 98 fits relatively snugly within the bore 30 formed in the conical sleeve 18 while another section of the body portion 98 fits relatively loosely within a bore 102 formed through the coil 34. The rearwardmost end of the body portion 98 is loosely contained within the bore 42 formed in the plug 36.

The probe in the present invention is made of a soft, magnetic material. It has been found that a hydrogen-annealed, Hy-Mu 80 alloy provides excellent results. The probe 32 described hereinabove and shown in the drawings is 1 mm in diameter by 20 mm long with a hemispherical outermost end. However, other shapes may also be utilized. For example, a spoon-shaped probe may be used as well as a probe with a hole therein that is similar to the eye of a needle. Hy-Mu 80 is an iron-nickel-molybdenum alloy having a very high initial magnetic permeability, high maximum permeability, low core loss and good magnetic shielding. A typical analysis for such an alloy found useful in the practice of this invention is given as follows:

| | |
|---|---|
| Carbon | 0.05% |
| Manganese | 0.05% |
| Silicon | 0.30% |
| Nickel | 80.0% |
| Molybdenum | 4.0% |
| Iron | balance |

These alloys are well known to those skilled in the art and are usually annealed in an oxygen-free, dry hydrogen atmosphere with a Dew Point below −40° F. for two to four hours at 2150° F. Then they are furnace cooled to 1100° F. and thereafter from 1100° F. to 700° F. cooled at a rate between 350° F. and 500° F. per hour.

These alloys found useful in our invention have the ability to return to less than 0.2% of the original magnetization after having been subjected to oerstad of direct current magnetizing force. This prevents magnetizeable objects in bodies such as eyes from adhering to the probe after the current flow is stopped as would be the case when conventional probes having high magnetic remanence are employed.

It will be evident from the foregoing that by depressing the pushbutton 90 the switch 54 will interconnect battery 74 and the coil 34 and thereby magnetize the tip 96 of the probe 32. Releasing the push button 90 will demagnetize the tip 96 in order to permit further manipulation of the instrument 10 so that the foreign body can easily be transferred to forceps or to another instrument.

There has been disclosed heretofore the best embodiment of the invention presently contemplated. However, it is to be understood that various changes and modifications may be made thereto without departing from the spirit of the invention.

What is claimed is:

1. A miniature surgical instrument particularly adapted for removing ferrous foreign particles from an eye, said instrument comprising:
   (a) a housing;
   (b) a magnetizable, axially elongated probe having a body portion that is at least partially contained within said housing and a tip portion extending outwardly therefrom wherein said tip portion is made of a hydrogen-annealed Hy-Mu 80 alloy;
   (c) coil means surrounding at least a part of said body portion of said probe;
   (d) switch means coupled to said coil and adapted to interconnect said coil to a source of electrical energy whereby said switch means may be operated to energize said coil to thereby magnetize said probe; and
   (e) battery means encompassed within said housing capable of providing electrical energy to energize said coil.

2. The surgical instrument according to claim 1 wherein the outer most end of said tip portion of said probe is hemispherical.

3. The surgical instrument according to claim 1 wherein said tip portion of said probe is approximately 1.0 mm in diameter.

4. The surgical instrument according to claim 1 wherein the length of said probe is approximately 20 mm.

5. The surgical instrument according to claim 1 wherein said probe is comprised of two concentric diametric sections defining said body portion and said tip portion, said body portion having a diameter greater than said tip portion.

6. The surgical instrument according to claim 1 wherein the outermost end of said tip portion of said probe is spoon-shaped.

7. The surgical instrument according to claim 1 wherein the outermost end of said tip portion of said probe has a hole therethrough.

8. The surgical instrument according to claim 1 wherein said housing comprises a central section having forward and rearward ends and a conical sleeve coupled to said forward end, said probe being integral with and extending coaxially out of the smaller end of said conical sleeve.

9. The surgical instrument according to claim 1 wherein said housing includes an external manually operable push button that is arranged to coact with said switch means.

* * * * *